United States Patent [19]

Buchanan

[11] Patent Number: 5,005,573
[45] Date of Patent: Apr. 9, 1991

[54] ENDOTRACHEAL TUBE WITH OXIMETRY MEANS

[76] Inventor: Dale C. Buchanan, 4217 Horseshoe Bend, Matthews, N.C. 28105

[21] Appl. No.: 556,947

[22] Filed: Jul. 20, 1990

[51] Int. Cl.[5] ............................................. A61M 16/04
[52] U.S. Cl. ................................ 128/207.14; 128/633; 128/634
[58] Field of Search ...................... 128/207.14, 200.26, 128/633, 634, 666, 665, 664, 637

[56] References Cited

U.S. PATENT DOCUMENTS

| | | |
|---|---|---|
| 3,335,715 | 8/1967 | Hugenholtz et al. |
| 3,690,769 | 9/1972 | Mori . |
| 3,807,390 | 4/1974 | Ostrowski et al. . |
| 4,444,185 | 4/1984 | Shugar ........................... 128/200.26 |
| 4,697,593 | 10/1987 | Evans et al. . |
| 4,824,242 | 4/1989 | Frick et al. . |
| 4,825,872 | 5/1989 | Tan et al. . |
| 4,928,687 | 5/1990 | Lampotang et al. ............ 128/207.14 |
| 4,928,691 | 5/1990 | Nicolson et al. ..................... 128/633 |
| 4,953,539 | 9/1990 | Nakamura et al. .................. 128/633 |

Primary Examiner—Edgar S. Burr
Assistant Examiner—Stephen R. Funk
Attorney, Agent, or Firm—Shefte, Pinckney & Sawyer

[57] ABSTRACT

An endotracheal breathing tube for use in surgical operations is equipped with a light emitting device adjacent its distal end to reside within the patient's trachea during use and with a compatible photosensitive detector positionable outside the patient's body in contact with the neck to intercept light transmitted from the light emitting device for performing accurate oximetry measurements and calculations of the patients's arterial blood oxygen saturation. In one embodiment, a light emitting diode is affixed to the distal portion of the tube body. In another embodiment, an optical fiber extends from a light emitting diode outside the patient's body through the tube to a fiber terminus at the distal location on the tube body.

7 Claims, 2 Drawing Sheets

FIG. 1

ENDOTRACHEAL TUBE WITH OXIMETRY MEANS

BACKGROUND OF THE INVENTION

The present invention relates broadly to surgical appliances and, more particularly, to oximetry devices for determining oxygen saturation in a surgery patient's arterial blood.

Over recent years, the measurement of arterial blood oxygen saturation, commonly referred to as oximetry, has come into increasingly widespread usage during surgical procedures as a means for monitoring and preventing undetected hypoxemia of the surgical patient. Essentially, oximetry measures the amount of oxygenated hemoglobin in the arterial blood of the patient as a percentage of the total hemoglobin in the blood.

Various devices, typically referred to as oximeters, are available for performing oximetry measurements. So-called noninvasive pulse oximeters are configured to attach to a patient's fingertip, earlobe or nose and are operable to transmit light of differing wave lengths or colors, typically in the red and infrared spectrums, into the body part and to detect the light transmitted therethrough or the light reflected thereby. It is known that the ability of blood hemoglobin to absorb light varies in relation to the level of oxygenation of the hemoglobin. Accordingly, detection of the reflected or transmitted light from a pulse oximeter indicates the amount of light absorbed, from which the arterial blood oxygen saturation can be calculated.

While non-invasive pulse oximeters of the aforementioned type provide substantial advantages over previous oximetry methods which required the withdrawal of blood samples from a patient, pulse oximeters are still subject to several disadvantages. First, when the patient is in a state of low blood perfusion, e.g. when the patient has lost a substantial amount of blood, is cold, or has peripheral vascular disease or for other reasons does not perfuse the extremities well, difficulty may often be experienced in obtaining a sufficient light transmission or reflectance signal from which to calculate the patient's arterial blood oxygen saturation. Likewise, ambient light sources and relative movement of the patient and the oximeter may also interfere with the accuracy of the measurements and calculations obtained.

During surgery under general anesthesia, it is standard practice to insert an endotracheal tube through the patient's mouth and into the trachea to connect the patient to a ventilator to assist breathing. It is well known that such an endotracheal tube is subject to movement and migration within the patient's trachea which poses a continual potential problem in maintaining correct placement and positioning of the tube within the patient's trachea. Accordingly, it is common practice upon initial insertion of an endotracheal tube for the anesthetist or anesthesiologist to check the patient for equal breathing sounds in both lungs, or to perform a chest radiograph of the patient, or to measure the length of the tube inserted past the patient's teeth or lips in comparison to pre-established norms, as a means of determining whether the tube has been properly positioned. Alternatively, some endotracheal tubes are provided with a metal band positioned to be detectable by a compatible sensor placed on the front of the patient's neck in the suprasternal notch when the tube is properly positioned. Under any of these methods, it is necessary to periodically perform the same check at appropriate intervals over the course of the surgical procedure to insure that the proper positioning of the tube is maintained. Disadvantageously, however, none of these tube placement methods enables continuous monitoring of the placement of the endotracheal tube.

SUMMARY OF THE INVENTION

It is accordingly an object of the present invention to provide a device which enables oximetry measurements and calculations to be performed during surgical procedures with improved accuracy over conventional noninvasive pulse oximeters. It is a particular object of the present invention to incorporate such oximetry device in an endotracheal tube to enable more accurate and more quickly responsive oximetry measurements to be made through the patient's neck while also simultaneously enabling continual monitoring of the tube position within the trachea.

Briefly summarized, the present invention provides an improved endotracheal tube for insertion within a surgical patient's trachea for assisting breathing during surgical and like procedures. According to the present invention, the tube is provided with an arrangement for transmitting light outwardly from a predetermined location on the tube which resides within the patient's trachea during use and a compatible arrangement for detecting light transmitted by the light transmitting arrangement. The detecting arrangement is manipulable outside the patient's body for selective positioning on the patient's neck in disposition for receiving light transmitted by the transmitting arrangement. A suitable arrangement is provided for operatively connecting the transmitting arrangement and the detecting arrangement with an oximeter for measuring oxygen saturation in the patient's arterial blood as a function of the transmitted light received by the detecting arrangement.

In one embodiment of the present invention, the transmitting arrangement includes a light emitting device, such as a light emitting diode, affixed to the endotracheal tube at the aforesaid predetermined location. Appropriate electrical wiring extends along the tube from a second predetermined location thereon which resides outside the patient's body during use to the first-mentioned predetermined location whereat the wiring is operatively connected to the light emitting device.

In an alternate embodiment, the light emitting device resides outside the patient's body and is operatively connected to an optical fiber which extends along the endotracheal tube to a light emitting terminus of the fiber at the aforesaid first predetermined location.

The detecting arrangement preferably includes a photosensitive device, such as a photodiode, detached from and manipulable independently of the endotracheal tube, the photosensitive device being operatively connected to the oximeter by suitable electrical wiring which is essentially unattached to the tube.

DESCRIPTION OF THE PREFERRED EMBODIMENT

Figure 1:
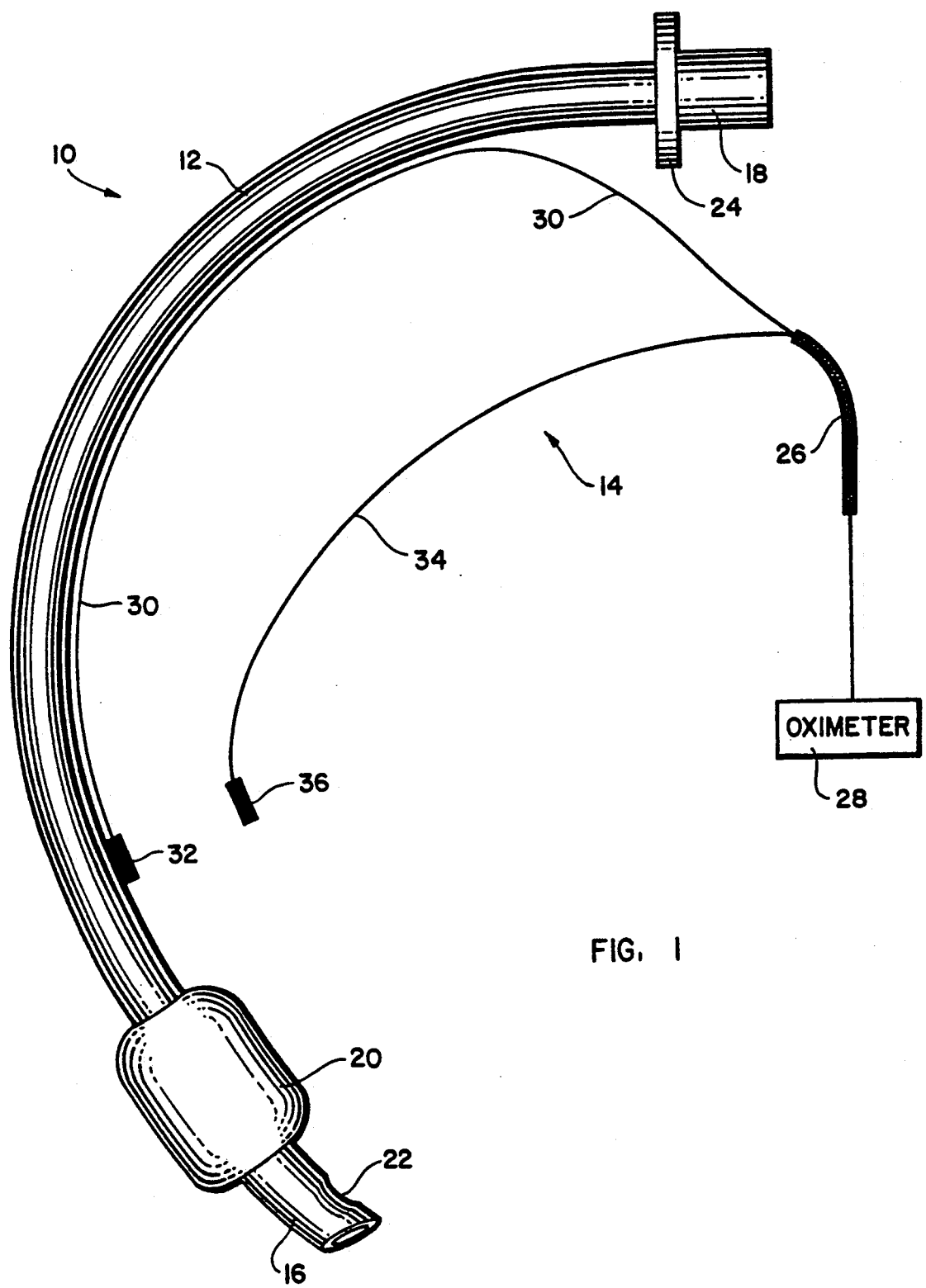
FIG. 1 is a schematic side elevational view of an endotracheal tube according to one preferred embodiment of the present invention.

Referring now to the accompanying drawings and initially to FIG. 1 an endotracheal tube according to the preferred embodiment of the present invention is generally indicated at 10. Basically, the endotracheal tube 10 includes a tube body 12 to which an oximetry measuring probe and sensor assembly, collectively indicated at 14, is affixed.

The tube body 12 may be of any conventional endotracheal tube construction, the tube body 12 illustrated in FIG. 1 being schematically representative of one common type of endotracheal tube. Basically, the tube body 12 is hollow along its entire length and is open at its opposite leading (distal) and trailing (proximal) ends 16,18, respectively. A radially outwardly expansible cuff 20, e.g., an inflatable balloon, is affixed exteriorly to the tube body 12 closely adjacent its leading end 16 and a side port 22 is formed through the annular wall of the tube body 12 intermediate the cuff 20 and the leading end 16. One or more appropriate passageways (not shown) are formed through the outer wall of the tube body 12 along its length and are connected to a suitable valve or the like (also not shown) for supplying and exhausting inflating air to and from the cuff 20. A radially outwardly projecting collar 24 is formed at a close spacing to the trailing end 18 of the tube body 12 to facilitate end-to-end connection of the trailing end 18 to a flexible hose (not shown) extending from a ventilator or other conventional breathing apparatus.

In use, the leading end 16 of the tube body 12 is inserted through a surgical patient's mouth and throat into the trachea within the patient's neck and, when properly positioned, the cuff 20 is inflated to assist in retaining the leading end 16 in its desired disposition within the trachea. The tube body 12 is of sufficient length that the trailing end 18 remains outside the patient's mouth, adhesive surgical tape typically being applied about the tube to the patient's mouth to essentially seal the patient's lips to the tube body 12. Upon connection of the trailing end 18 of the tube body 12 to a breathing apparatus, a controlled supply of oxygen can be delivered to the patient during surgery.

The oximetry measuring probe and sensor assembly 14 includes a connection cable 26 by which the assembly 14 is connectable to an oximetry measuring and calculation unit, only representatively indicated at 28, which may be of any conventional construction. The connection cable 26 includes a first electrical lead wire 30 affixed to or embedded in the annular wall of the tube body 12 to extend from a proximal location closely adjacent the collar 24, which location resides outside the patient's body during use, to a distal location closely adjacent the cuff 20, which location resides within the patient's trachea during use, whereat the lead wire 30 is operatively connected to one or more light emitting devices 32, preferably in the form of light emitting diodes. The connection cable 26 also includes a second electrical lead wire 34 which extends outwardly from the cable 26 without connection to the tube body 12 and is operatively connected at its extending free end to one or more photosensitive devices 36, preferably in the form of photodiodes.

In operation, the light emitting diode or diodes 32 are operatively controlled by the oximetry device 2 to emit light in a direction radially outwardly from the tube body 12 and the photodiode 36 is adapted to receive and detect light transmitted by the light emitting diode or diodes 32 when the photodiode or photodiodes 36 are positioned within the path of transmitted light. The lead wire 34 is flexible so as to enable the photodiode or photodiodes 36 to be freely movable and manipulable for placement of the photodiode or photodiodes 36 at an location on the anterior surface of the patient's neck to intercept light transmitted by the light emitting diode or diodes 32 on the distal portion of the tube body 12 within the patient's trachea. Once the photodiode or photodiodes 36 are positioned to detect transmitted light from the light emitting diode or diodes 32, the photodiode or photodiodes 36 are finally positioned to maximize the light reception and, thereafter, are maintained in direct contact with the skin of the patient's neck, e.g. by surgical tape.

Thus, upon initial insertion of the tube body 12 into the trachea of a surgical patient, the light emitting diode or diodes 32 and the photodiode or photodiodes 36 enable the disposition of the leading (distal) end of the tube body 12 within the patient's trachea to be detected and, in turn, to be precisely positioned where desired. Likewise, throughout the ensuing surgical operation, the positioning of the leading end 16 can be continuously monitored. Simultaneously, the oximetry measuring and calculation device 28 compares the amount or intensity of light detected by the photodiode or photodiodes 36 with the amount or intensity of light transmitted by the light emitting diode or diodes 32 to obtain a measurement of the amount of light absorbed by the hemoglobin in the blood passing through the intervening arteries through the patient's neck. In conventional fashion, the oximetry device controls the light emitting diode or diodes 32 to transmit both red and infrared light in performing such measurements and, from such measurements calculates the level of arterial blood oxygen saturation for the patient.

Advantageously, since the human body automatically preserves blood flow through the arteries in the neck to the brain at the cost of blood flow to the extremities or more peripheral skin regions, the blood oxygen saturation measurements and calculations obtained by light transmission through the neck under the present invention will not only be more accurate but also more quickly responsive to oxygen saturation changes than with conventional pulse oximetry devices attachable to a patient's fingertip, earlobe, or nose. At the same time, the artifact associated with ambient light will affect the oximetry calculations under the present invention to a substantially lesser degree than with conventional pulse oximeters. Further, as aforementioned, the provision of an oximetry light emitting device on an endotracheal tube in accordance with the present invention enables the positioning of the tube within the patient's trachea to be continuously monitored over the entire course of a surgical procedure.

Figure 2:
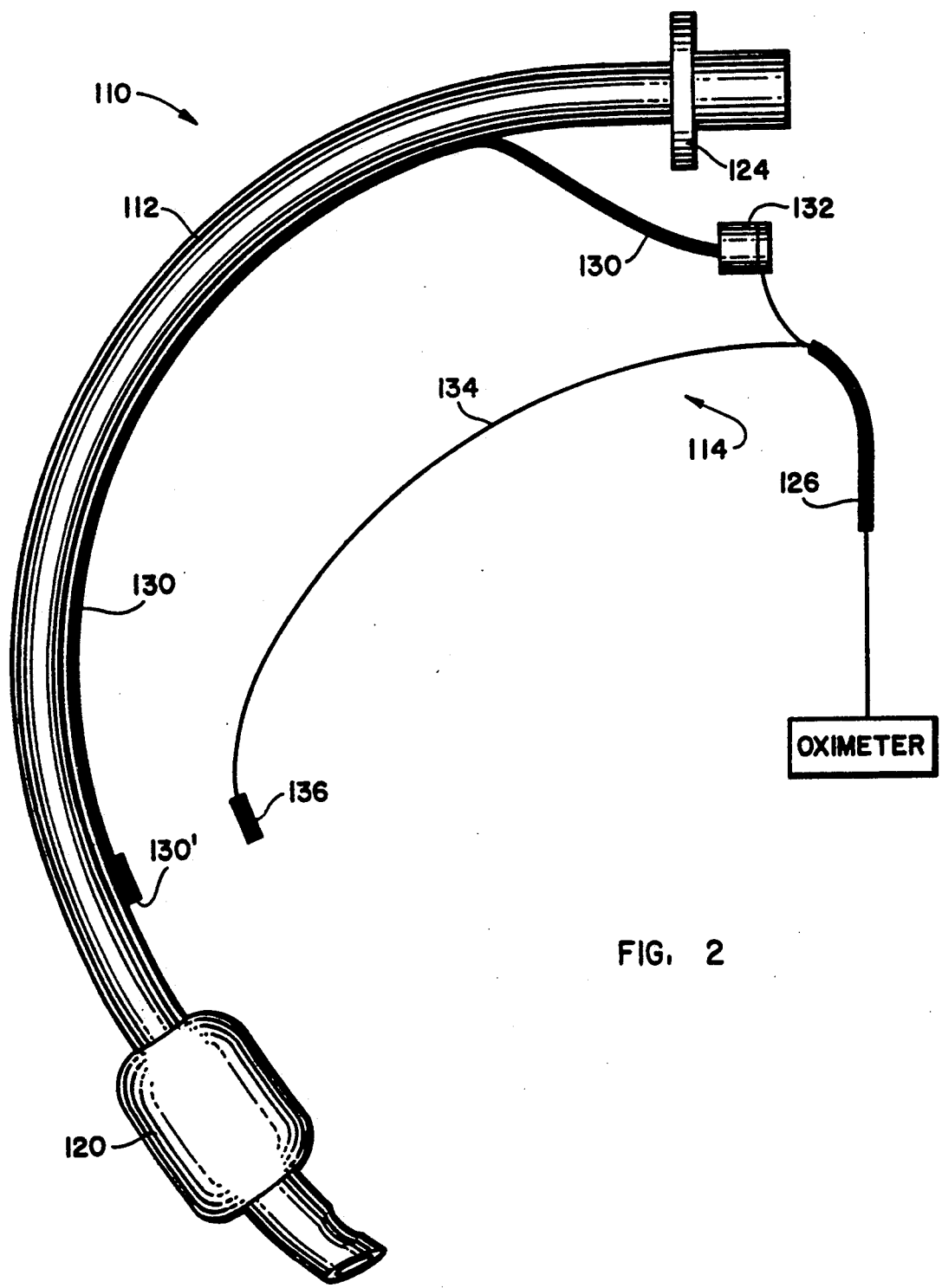
FIG. 2 is another schematic side elevational view, similar to FIGURE depicting an alternative embodiment of endotracheal tube according to the present invention.

Referring now to FIG. 2, an alternative embodiment of the endotracheal tube of the present invention is indicated generally at 110 and basically includes a tube body 112 identical to that of the embodiment of FIG. 1 with an alternative form of oximetry measuring probe and sensor assembly 114. In this embodiment, the oximetry probe and sensor assembly 114 utilizes a light emitting diode or other light emitting device 132 disposed outside the patient's body and a flexible light-transmitting optical fiber 130 connected to and extending from the light emitting diode 132 through the annular wall of the tube body 112 from a proximal location closely adjacent the tube collar 124 to a distal location closely adjacent the tube cuff 120 whereat a terminus 130' of the optical fiber 130 is exposed at the exterior surface of the tube body 112 for transmitting light radially outwardly therefrom. The light emitting diode 132 is electrically connected to a connection cable 126 along with a lead wire 134 to a photodiode 136 substantially identically to that of the embodiment of FIG. 1 for selective manipulation and positioning to intercept light transmitted from the optical fiber terminus 130'. As will thus be understood, operation of the endotracheal tube 110 and the attendant advantages thereof are the same as described above for the endotracheal tube 10.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. In an endotracheal tube for insertion within a surgical patient's trachea for assisting breathing during surgical and like procedures, the improvement comprising means for transmitting light outwardly from a predetermined location on said tube which resides within the patient's trachea during use, means for detecting light transmitted by said transmitting means, said detecting means being manipulable outside the patient's body for selective positioning on the patient's neck in disposition for receiving light transmitted by said transmitting means, and means for operatively connecting said transmitting means and said detecting means with an oximeter for measuring oxygen saturation in the patient's arterial blood as a function of the transmitted light received by said detecting means.

2. The improved endotracheal tube of claim 1 and characterized further in that said transmitting means comprises a light emitting device affixed to said tube at said predetermined location.

3. The improved endotracheal tube of claim 2 and characterized further in that said oximeter connecting means comprises electrical wiring means extending along said tube from another predetermined location on said tube which resides outside the patient's body during use to said first-mentioned predetermined location and operatively connected thereat to said light emitting device.

4. The improved endotracheal tube of claim 3 and characterized further in that said light emitting device comprises a light emitting diode.

5. The improved endotracheal tube of claim 1 and characterized further in that said detecting means comprises a photosensitive device detached from and manipulable independently of said tube and said oximeter connecting means comprises electrical wiring means operatively connected to said photosensitive device.

6. The improved endotracheal tube of claim 1 and characterized further in that said transmitting means comprises an optical fiber having a light emitting terminus at said predetermined location and extending therefrom to another predetermined location on said tube which resides outside the patient's body during use, and a light emitting device operatively connected to said optical fiber for directing light to travel along said optical fiber.

7. The improved endotracheal tube of claim 6 and characterized further in that said light emitting device comprises a light emitting diode.

* * * * *